United States Patent
Maskara et al.

(10) Patent No.: US 9,089,710 B2
(45) Date of Patent: Jul. 28, 2015

(54) SYSTEMS AND METHODS TO OPTIMIZE PACING FUSION WITH NATIVE ACTIVATION

(71) Applicant: Cardiac Pacemakers, Inc., St. Paul, MN (US)

(72) Inventors: Barun Maskara, Blaine, MN (US); Allan C. Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/086,515

(22) Filed: Nov. 21, 2013

(65) Prior Publication Data

US 2014/0188184 A1    Jul. 3, 2014

Related U.S. Application Data

(60) Provisional application No. 61/746,631, filed on Dec. 28, 2012.

(51) Int. Cl.
  *A61N 1/00* (2006.01)
  *A61N 1/368* (2006.01)
  *A61N 1/362* (2006.01)
  *A61N 1/365* (2006.01)

(52) U.S. Cl.
  CPC ............ *A61N 1/3682* (2013.01); *A61N 1/3627* (2013.01); *A61N 1/3684* (2013.01); *A61N 1/36564* (2013.01)

(58) Field of Classification Search
  CPC .................................................. A61N 1/36585
  USPC ....................................................... 607/9, 18
  See application file for complete search history.

(56) References Cited

U.S. PATENT DOCUMENTS

| 5,626,620 | A | 5/1997 | Kieval et al. |
| 6,507,756 | B1 | 1/2003 | Heynen et al. |
| 7,177,688 | B2 | 2/2007 | Salo et al. |
| 7,254,442 | B2 | 8/2007 | Van Gelder et al. |
| 8,116,866 | B2 | 2/2012 | Yonce et al. |

(Continued)

FOREIGN PATENT DOCUMENTS

| WO | WO-2005007075 A2 | 1/2005 |
| WO | WO-2014105306 A1 | 7/2014 |

OTHER PUBLICATIONS

"International Application Serial No. PCT/US2013/071247, International Search Report mailed Feb. 24, 2014", 5 pgs.

(Continued)

*Primary Examiner* — Amanda Patton
*Assistant Examiner* — Nadia A Mahmood
(74) *Attorney, Agent, or Firm* — Schwegman Lundberg & Woessner, P.A.

(57) ABSTRACT

In an example, a pacing therapy can be optimized using information indicative of an offset duration between an intrinsic first atrioventricular delay of a subject at rest and a second atrioventricular delay specified to enhance a cardiac output of the subject heart when the subject is at rest. Optimizing the therapy can include receiving information about a heart rate of the subject and receiving information about an intrinsic, heart rate dependent atrioventricular delay. In an example, a therapy parameter, such as a therapy atrioventricular delay, can be adjusted using information about the received heart rate of the subject, the heart-rate-dependent third AV delay, or the offset duration.

20 Claims, 7 Drawing Sheets

(56) References Cited

U.S. PATENT DOCUMENTS

| | | |
|---|---|---|
| 8,214,041 B2 | 7/2012 | Van Gelder et al. |
| 2004/0193223 A1 | 9/2004 | Kramer et al. |
| 2005/0107837 A1* | 5/2005 | Salo et al. ............ 607/9 |
| 2005/0137632 A1 | 6/2005 | Ding et al. |
| 2005/0209650 A1 | 9/2005 | Van Gelder et al. |
| 2006/0235478 A1 | 10/2006 | Van Gelder et al. |
| 2008/0269823 A1 | 10/2008 | Burnes et al. |
| 2009/0149904 A1 | 6/2009 | Perschbacher et al. |
| 2009/0275999 A1 | 11/2009 | Burnes et al. |
| 2009/0292334 A1 | 11/2009 | Rom |
| 2010/0087889 A1 | 4/2010 | Maskara et al. |
| 2011/0160787 A1 | 6/2011 | Greenhut et al. |
| 2011/0178567 A1 | 7/2011 | Pei et al. |
| 2011/0196440 A1 | 8/2011 | Koh |

OTHER PUBLICATIONS

"International Application Serial No. PCT/US2013/071247, Written Opinion mailed Feb. 24 2014", 8 pgs.

* cited by examiner

| HEART RATE (BPM) | HEART RATE DEPENDENT INTRINSIC AV DELAY (ms) |
|---|---|
| 70 | 150 |
| 80 | 135 |
| 90 | 120 |
| 100 | 110 |
| 110 | 105 |

| HEART RATE (BPM) | INTRINSIC AV DELAY (ms) | THERAPY AV DELAY (E.G., THERAPY AC DELAY = RV-LV DELAY (-30ms) + INTRINSIC AV DELAY) |
|---|---|---|
| 70 | 150 | 120 |
| 80 | 135 | 105 |
| 90 | 120 | 90 |
| 100 | 110 | 80 |
| 110 | 105 | 75 |

SYSTEMS AND METHODS TO OPTIMIZE PACING FUSION WITH NATIVE ACTIVATION

CLAIM OF PRIORITY

This application claims the benefit of priority under 35 U.S.C. §119(e) of U.S. Provisional Patent Application Ser. No. 61/746,631, filed on Dec. 28, 2012, which is herein incorporated by reference in its entirety.

BACKGROUND

The sinoatrial node is an intrinsic pacemaker of the heart that generates electrical signals that can propagate through a cardiac electrical conduction system to various regions of the heart, such as to initiate contraction of cardiac muscle tissues. Some subjects experience conduction defects in the native electrical conduction systems of the heart. Such defects can manifest as uncoordinated or irregular cardiac function of one or more chambers of the heart. For example, in a subject with left bundle branch block (LBBB), electrical pulses may not be conducted normally along left bundle branches of the heart. This can result in a delayed activation of a left ventricle, such as with respect to a right ventricle. Thus, an LBBB can cause dyssynchrony between the left and right ventricles of the heart.

In various examples, cardiac rhythm management (CRM) systems can be used to treat cardiac dysfunction, such as to treat bundle branch block. Some CRM systems can include an implantable medical device configured to deliver electrical stimulation signals to one or more ventricles of the heart to facilitate resynchronization of the ventricles or otherwise improve cardiac function. For example, Pei et al., in U.S. Patent Publication No. 2011/0178567, entitled "TECHNIQUES FOR PROMOTING BIVENTRICULAR SYNCHRONY AND STIMULATION DEVICE EFFICIENCY USING INTENTIONAL FUSION," refers to a method for pacing a ventricle having slowed atrioventricular conduction. Van Gelder et al., in U.S. Pat. No. 7,254,442, entitled "APPARATUS AND METHOD FOR "LEPARS" INTERVAL-BASED FUSION PACING," refers to a method of LV-only fusion pacing therapy for a non-synchronous pair of ventricles.

OVERVIEW

Cardiac pacing parameters, such as an atrioventricular (AV) delay, can be adjusted to optimize a therapy to accommodate changes in a patient or subject physiology (e.g., in response to a subject physical activity level change, or a drug regime change, etc.). In an example, a system or method can include determining an AV delay for a cardiac pacing therapy, such as at multiple heart rates for a subject or subject population to optimize cardiac performance at multiple heart rates. In an example, information about an intrinsic AV delay at rest can be used to determine an AV delay parameter for use in a subject therapy, such as when a subject is not at rest.

Some examples can include systems or methods for dynamically adjusting a pacemaker AV delay. In an example, a pacemaker AV delay can be used in a pacing therapy for one or more ventricles, such as to optimize fusion of a paced ventricular event (e.g., a ventricular contraction in response to an electrostimulation signal) with an intrinsic, or native ventricular activation at varying heart rates of the subject. By optimizing pacing fusion in a heart rate dependent manner, cardiac function may be enhanced, such as by improving cardiac output over a range of subject heart rates.

In an example, a method for adjusting a pacing therapy can include receiving information indicative of an offset duration difference between an intrinsic first AV delay of a subject at rest and a second AV delay specified to enhance a cardiac output of the subject heart when the subject is at rest. The method can include receiving information about a heart rate of the subject. The method can include adjusting a pacing therapy using information about the received heart rate of the subject, a heart rate dependent third AV delay (e.g., a heart rate dependent intrinsic AV delay), and the offset duration.

In an example, a system can be configured to adjust a pacing therapy in a ventricle of a subject heart, such as a left ventricle. The system can include a therapy control circuit, a therapy output circuit, or a physiologic parameter sensing circuit. The therapy output circuit can be coupled to the therapy control circuit and can be configured to generate the pacing therapy. The therapy output circuit can be coupleable to a therapy delivery electrode, and the physiologic parameter sensing circuit can be configured to receive information indicative of a subject heart rate. The therapy control circuit can be configured to use an intrinsic first AV delay of a subject at rest, a second AV delay specified to enhance a cardiac output of a subject heart when the subject is at rest, and a heart-rate-dependent third AV delay, to configure the therapy output circuit to generate a pacing therapy.

This overview is intended to provide an overview of subject matter of the present patent application. It is not intended to provide an exclusive or exhaustive explanation of the disclosure. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
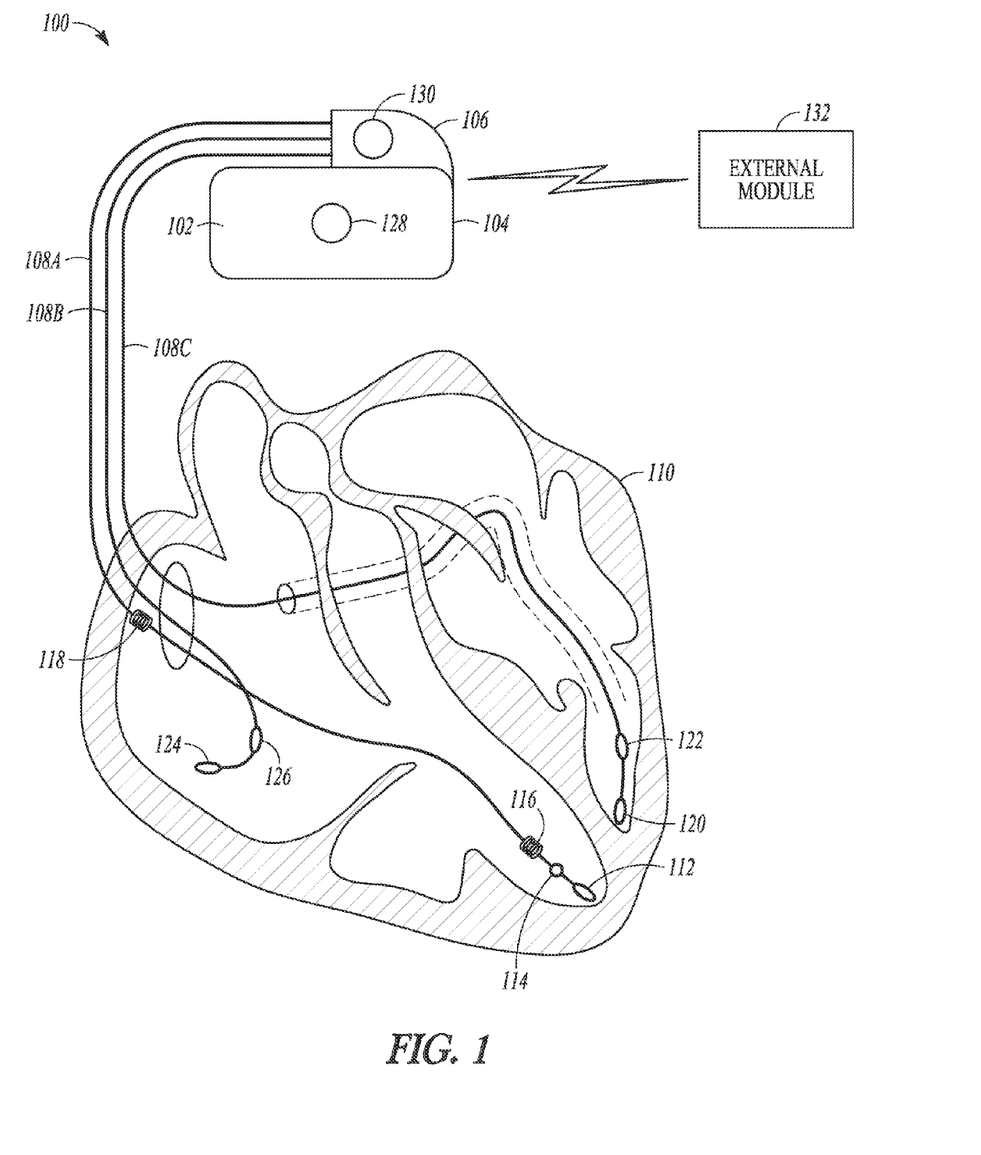
FIG. 1 illustrates generally an example of a Cardiac Rhythm Management (CRM) system.

FIG. 1 illustrates generally an example of a cardiac rhythm management (CRM system 100 and an environment in which the CRM system 100 can be used. The CRM system 100 can include an implantable medical device (IMD) 102 coupled to a heart 110. In an example, the IMD 102 can be configured to receive or determine a therapy atrioventricular (AV) delay parameter that can be used to provide a pacing therapy to a ventricle of the heart 110, such as to treat a bundle branch block. In an example, the therapy AV delay parameter can include information about a duration that can be used by the IMD 102 to time or coordinate a therapy. For example, the therapy AV delay parameter can include information about an interventricular delay. In an example, a therapy delivered by the IMD 102 to the heart 110 can initiate an activation of a left ventricle (LV) of the heart 110, such as in coordination with an intrinsic activation of a right ventricle (RV) of the heart 110; however, it is also contemplated that the therapy delivered by the IMD 102 to the heart 110 can initiate an activation of a right ventricle (RV) of the heart 110, such as in coordination with an intrinsic activation of a left ventricle (LV) of the heart 110. In an example, such coordinated, or fused, therapies can increase cardiac output of the heart 110.

In an example, the IMD 102 that can include a hermetically-sealed housing 104 and a header 106 extending from the housing 104. The header 106 can include one or more ports for receiving one or more leads, such as an implantable lead 108A, a lead 108B, and a lead 108C (collectively referred to herein as leads 108). The distal portions of the leads 108 can include one or more sensors or electrodes, such as including electrodes that can be used to deliver an electrostimulation signal (e.g., a pacing energy and/or a defibrillation energy) to the heart 110. The leads 108 and electrodes can be used to sense electrical activity of the heart 110, including electrical activity related to contractions of the atria or ventricles.

In an example, the lead 108A can be configured to be disposed in a right ventricle (RV) of a subject. The lead 108A can extend from a superior vena cava (SVC) to a right atrium (RA), and then into the RV. The lead 108A can include an RV tip electrode 112, an RV ring electrode 114, a RV shock coil electrode 116, and an RA or SVC shock coil electrode 118, among other electrodes or sensors. In an example, the lead 108B can be configured to be disposed in an LV of a subject. The lead 108B can extend from an SVC to an RA, and through the coronary sinus into the coronary vasculature, such as near a portion of the LV. In an example, an implantable or subcutaneous lead can include one or more electrodes and/or sensors. In the example of FIG. 1, the lead 108B can be an implantable lead that includes a distal electrode 120 and a proximal electrode 122, among other electrodes or sensors. In an example, the lead 108C can be configured to be disposed in an atrium of a subject heart. The RA lead 108C can extend from the SVC into the RA, and can include a distal electrode 124 and a proximal electrode 126, among other electrodes or sensors. In an example, other electrodes (e.g., a housing electrode 128 on the housing 104, a header electrode 130 on the header 106, an epicardial electrode, a subcutaneous electrode located away from the heart, or an electrode located elsewhere) can be used to provide electrostimulation to the heart 110 or sense electrical activity of the heart 110.

In an example, multiple different electrode configurations can be used in the CRM system 100. In an example, an RA-Can electrode configuration can be used to deliver an electrostimulation signal using an RA-ring electrode and an electrode disposed on the can housing 104. In an example, a voltage can be sensed, such as using an RA-tip electrode and the can housing 104. Other configurations can include, but are not limited to, RV-Can (e.g., using electrodes on the RV lead 108A and the can housing 104 for stimulation and sensing), LV-Can (e.g., using electrodes on the LV lead 108B and the can housing 104 for stimulation and sensing), RA-LV-Can (e.g., using electrodes on the RA lead 108C, LV lead 108B and the can housing 104 for stimulation and sensing), RV-LV (e.g., using electrodes on the RV lead 108A and the LV lead 108B for sensing and stimulating), and the like. The electrodes can be configured to deliver cardioversion, defibrillation, pacing, or resynchronization therapies, among other therapies, such as to at least one ventricle of the heart 110.

In an example, the IMD 102 can communicate with one or more other devices, such as wirelessly or using a wired connection. The IMD 102 can communicate unidirectionally or bidirectionally with an external module 132, such as a programmer, repeater, or other handheld device, among others. In an example, the external module 132 can be used to configure or program one or more parameters or settings in the IMD 102. For example, the external module 132 can be used to update therapy parameters such as an AV delay, threshold value (e.g., sensing threshold value, pacing threshold value, or lead impedance value), or a pacing signal parameter. The external module 132 can be used to select a therapy mode, to initiate a subject therapy, or to identify an arrhythmia. In an example, the external module 132 can be configured to communicate with a remote server (not shown in the figure), such as can be used to remotely provide data to or receive data from the IMD 102.

In an example, the IMD 102 can include or can be coupled to one or more physiologic sensors, such as can be configured to receive information indicative of a subject physiologic status. A physiologic sensor can include a pressure sensor, accelerometer, fluid flow sensor, heart rate sensor, heart sound sensor, blood chemistry sensor, or physical activity level sensor, among others. In an example, the IMD 102 can be configured to monitor a subject heart rate, blood pressure, blood chemistry, respiration, or a physical activity level of a subject using information received from a physiologic sensor, and the IMD 102 can be configured to responsively use the received information to control a subject therapy.

In an example, a cardiac conduction block, such as a bundle branch block (e.g., a left bundle branch block (LBBB) or a right bundle branch block (RBBB)) can be identified using a device-based electrogram (EGM), such as received from electrodes on the leads 108, or using electrocardiography (ECG) signals received from one or more surface electrodes. In an example, in response to identifying a bundle branch block (e.g., automatically using the IMD 102), a therapy can be initiated or configured, such as using the external module 132 to program the IMD 102 to provide a therapy to address an arrhythmia.

In an example, the IMD 102 can be configured to provide an LV-only pacing therapy to address a left bundle branch conduction block. In an example, the IMD 102 can be configured to provide an RV-only pacing therapy to address a right bundle branch conduction block. In an example, the IMD 102 can be configured to provide a pacing therapy to one or more portions (e.g., LV or RV) of the heart 110 such that a paced activation of the one or more portions of the heart 110 can coincide with a native activation of the same or different portion(s) of the heart 110, such that the paced activation can be said to be "fused" with the native activation. In an example, the IMD 102 can be configured to calculate a therapy AV delay that can be used to provide a pacing therapy to a ventricle of the heart 110, such as to treat a bundle branch block. In an example, the therapy can initiate an activation of the LV of the heart 110 in coordination with an intrinsic activation of the RV of the heart 110. In an example, such coordinated, or fused, therapies can increase cardiac output of the heart 110.

Figure 2:
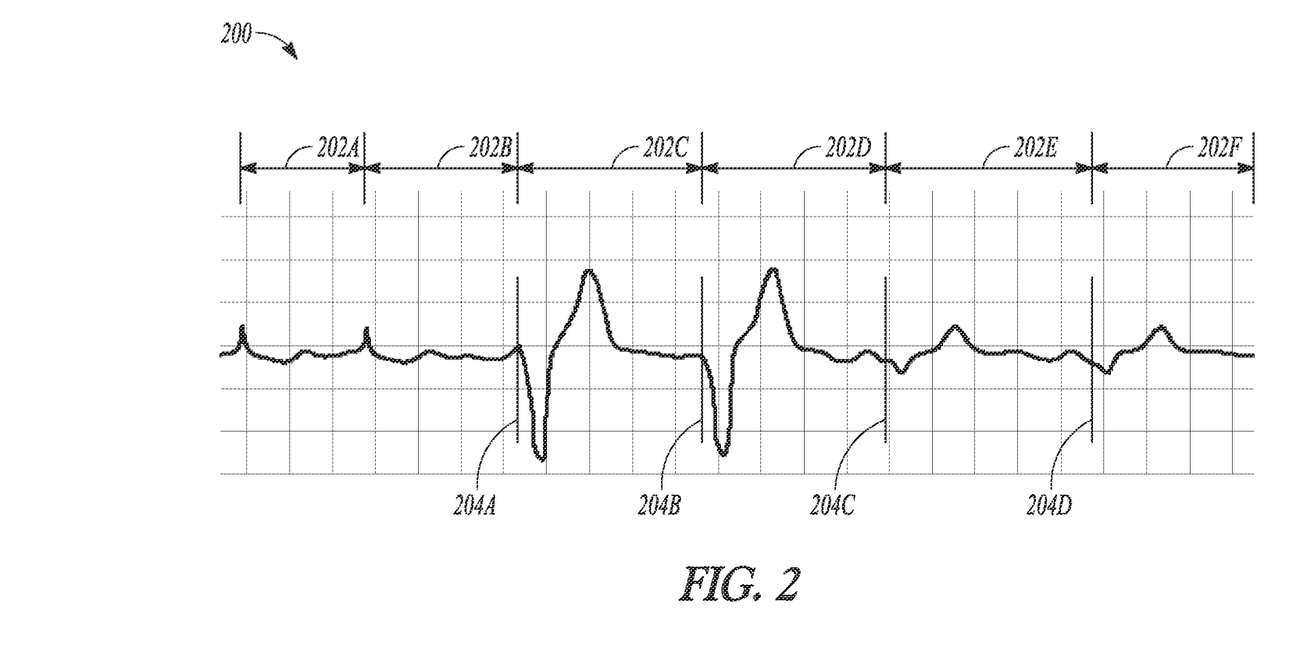
FIG. 2 illustrates generally an example of an electrocardiogram.

FIG. 2 illustrates generally an example of a portion of an electrocardiogram 200. The electrocardiogram 200 illustrates generally several components of a signal sensed over multiple cardiac cycles, including a first signal component 202a, a second signal component 202b, a third signal component 202c, a fourth signal component 202d, a fifth signal component 202e, and a sixth signal component 202f. The first and second signal components 202a and 202b illustrate generally examples of sensed atrial events, such as without a corresponding subsequent ventricular event. Electrocardiogram signals such as the first and second signal components 202a and 202b can indicate a cardiac arrhythmia because the signals indicate that one or more ventricles are not adequately depolarizing. In an example, a conduction block (e.g., LBBB or RBBB) can cause such an inadequate, improper, or delayed depolarization of a ventricle. In an example, in response to identifying an electrocardiogram signal indicative of a cardiac dysfunction, such as a conduction block, the IMD 102 can be configured to initiate a therapy, such as a pacing therapy. For example, the IMD 102 can be configured to deliver a pacing therapy, including delivering electrostimulation pulses to one or more ventricles (e.g., LV, RV, or both), such as to treat a cardiac arrhythmia or improve cardiac output.

In the example of FIG. 2, artifacts of a pacing or electrostimulation therapy can appear in the electrocardiogram 200. For example, a first spike 204a, a second spike 204b, a third spike 204c, and a fourth spike 204d are shown in the electrogram 200. In an example, the third and fourth signal components 202c and 202d can indicate ventricular depolarizations, such as can be evoked in response to an electrostimulation provided by the IMD 102. In the example of FIG. 2, the third and fourth signal components 202c and 202d include the first and second pacing spikes 204a and 204b, respectively, indicative of a relative timing of the electrostimulations.

In an example, an electrostimulation or pacing signal can be delivered (e.g., using the IMD 102 and the leads 108) to the heart 110 such that non-intrinsic activation of one or more portions of the heart 110 can be fused with intrinsic activation of other portions of the heart 110. Referring again to the example of FIG. 2, the third and fourth spikes 204c and 204d correspond to electrostimulation signals delivered to the heart 110. Delivery of the electrostimulation signals can be timed such that a depolarization of the first ventricle (e.g., in response to the electrostimulation signals) can be fused with an intrinsic depolarization of a second ventricle. In an example, a pacing therapy can be delivered to the LV of the heart 110, and the resulting depolarization of the LV can be fused with the intrinsic depolarization of the RV, such as to treat a left bundle branch block.

In an example, a pacing therapy can be delivered to the RV of the heart 110, and the resulting depolarization of the RV can be fused with an intrinsic depolarization of the RV, such as to treat a right bundle branch block. In an example, both ventricles can be paced, such as to fuse the ventricles with an intrinsic depolarization of the atrium. In the example of FIG. 2, the fifth and sixth signal components 202e and 202f illustrate examples of electrocardiogram signals sensed in response to electrostimulation signals (e.g., in response to electrostimulation signals represented by the spikes 204c and 204d, respectively) that are timed to fuse evoked ventricular events with native activation of the heart 110.

Figure 3:
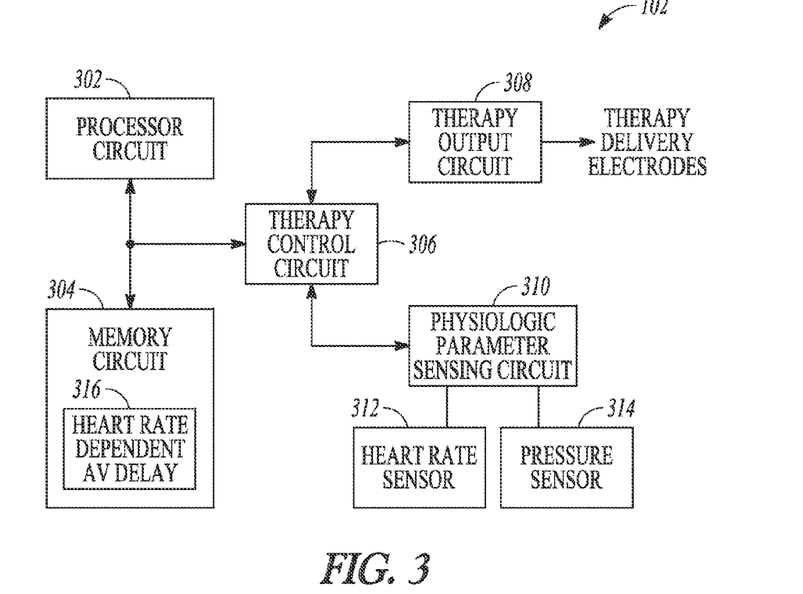
FIG. 3 illustrates generally an example of portions of an implantable medical device (IMD) for delivering a pacing therapy.

FIG. 3 illustrates generally an example of a portion of the IMD 102. In the example of FIG. 3, the IMD 102 includes a processor circuit 302, a memory circuit 304, a therapy control circuit 306, a therapy output circuit 308 and a physiologic parameter sensing circuit 310. The therapy control circuit 306 can be communicatively coupled to the processing circuit 302, the memory circuit 304, the therapy output circuit 308 and the physiologic parameter sensing circuit 310. In an example, the processor circuit 302 can be configured to execute operating instructions (e.g., received from the memory circuit 304) for the therapy control circuit 306, and can be integrated with the therapy control circuit 306.

The therapy control circuit 306 can be configured to control a delivery of one or more therapies, such as a pacing therapy, such as generated by the therapy output circuit 308. In an example, the therapy control circuit 306 can use information received from the physiologic parameter sensing circuit 310 to initiate or adjust a subject therapy. In an example, the physiologic parameter sensing circuit 310 can be coupled to one or more sensors, such as a heart rate sensor 312, or a pressure sensor 314, among others, to receive information about a subject heart rate. In an example, the memory circuit 304 can be configured to store device or therapy parameters, including information about an AV delay (e.g., information about an intrinsic AV delay duration or information about a therapy AV delay parameter). In an example, the memory circuit 304 can be configured to store subject-specific information about an intrinsic heart rate dependent AV delay 316.

The therapy output circuit 308 can be configured to generate an electrostimulation therapy and provide a therapy to one or more output terminals. The therapy output circuit 308 output terminals can be coupled to one or more therapy delivery electrodes (e.g., via the leads 108). In an example, the therapy delivery electrode can be disposed in the LV of the heart 110 such that the therapy output circuit 308 can be configured to deliver a pacing therapy to the LV of the heart 110. For example, the therapy output circuit 308 can be configured to deliver a pacing therapy to the LV using electrodes such as the distal electrode 120 and the proximal electrode 122 of the LV lead 108B, however, other electrode combinations can be used to deliver the pacing therapy to the LV.

In an example, a therapy delivery electrode can be disposed in the RV of the heart 110, and the therapy output circuit 308 can be configured to deliver a pacing therapy to the RV of the heart 110. For example, the therapy output circuit 308 can be configured to deliver the pacing therapy to the RV using electrodes such as the RV tip electrode 112, the RV ring electrode 114, and the RV shock coil electrode 116 of the RV lead 108A, however, other electrode combinations can be used to deliver the pacing therapy to the RV. In an example, a therapy delivery electrode can be disposed in an atrium of the heart 110, and the therapy output circuit 308 can be configured to deliver a pacing therapy to the atrium of the heart 110. In an example, the therapy output circuit 308 can be configured to provide a pacing therapy to the RA using distal electrode 124 and proximal electrode 126 of the RA lead 108C, however, other electrode combinations can be used to deliver the pacing therapy to the RA.

In an example, the physiologic parameter sensing circuit 310 can be configured to use physiologic subject information to identify or distinguish intrinsic and non-intrinsic cardiac events. For example, the physiologic parameter sensing circuit 310 can be configured to identify or distinguish an intrinsic atrial event, an intrinsic ventricular event, a non-intrinsic atrial event, and a non-intrinsic ventricular event. In an example, a non-intrinsic event can include a depolarization (or partial depolarization) of one or more portions of the heart, such as in response to an electrostimulation signal (e.g., delivered using the therapy output circuit 308 or another device).

In an example, the physiologic parameter sensing circuit 310 can be configured to receive heart rate information about the subject, such as using the heart rate sensor 312. In an example, the IMD 102 can be configured to determine heart rate of the subject when the subject is at rest, such as using the physiologic parameter sensing circuit 310 and the heart rate sensor 312. That is, a subject heart rate can be determined when the subject is in a resting state and not undergoing any physical activity expected to increase or decrease the heart rate of the subject.

In an example, the therapy control circuit 306 can be configured to use or determine information about an intrinsic first atrioventricular (AV) delay, such as an AV delay corresponding to a subject heart when the subject is at rest. In an example, the intrinsic first AV delay can correspond to duration between a paced or sensed atrial event and a subsequent sensed event in a first ventricle of the subject heart when the subject is at rest. In an example, the intrinsic first AV delay can be determined using electrogram (EGM) signals sensed by the IMD 102 or diagnostic data from other sources, such as surface electrocardiogram (ECG) devices, when the subject is at rest.

In an example, the therapy control circuit 306 can be configured to use or determine information about a second AV delay when the subject is at rest. The second AV delay can be an AV delay configured to enhance a cardiac output (e.g., to increase stroke volume) of the subject, such as by improving or enhancing coordination of one or more areas of the heart 110. The second AV delay can correspond to a duration between a paced or sensed atrial event and a paced event in a second ventricle of the subject heart when the subject is at rest (e.g., in a ventricle other than the ventricle that corresponds to the intrinsic first AV delay). That is, the second AV delay can correspond to a duration at which the second ventricle can be paced such that the paced activation of the second ventricle can enhance cardiac output when the subject is at rest.

In an example, the second AV delay can be determined using a pressure catheter disposed in the second ventricle of the heart 110. In an example, the second AV delay can be determined using Doppler echocardiography using ultrasound to deter one or more hemodynamic parameters of the heart 110. For example, the pressure catheter or the Doppler echocardiography can be used to determine a hemodynamic parameter such as a change in pressure over change in time (dP/dT) for the second ventricle. The therapy control circuit 306 can be configured to select a particular AV delay value as the second AV delay for which the (dP/dT) has an elevated value (e.g., a maximum value), such as when the subject is at rest. In an example, the second AV delay can be updated in response a subject physiologic event or in response to a threshold change in a physiologic status of the subject. For example, on detection of an increase in an atrial rate of the subject, the second AV delay can be updated, such as to maintain the cardiac output of the heart 110.

In an example, the therapy control circuit 306 can be configured to adjust a therapy for a subject with a cardiac conduction block, such as an LBBB. For example, the therapy control circuit 306 can be configured to deliver a pacing therapy in an LV-only pacing mode. In this example, the intrinsic first AV delay can be determined using a duration between a sensed or paced atrial event and a subsequent sensed event in the RV of the heart 110. The second AV delay can be determined using a duration between a sensed or paced atrial event and a subsequent paced event in the LV of the heart 110, such as when the subject is at rest. In an example, the second AV delay can be selected such that the paced event of the LV is closely fused with the intrinsic event of the RV of the heart 110, such as to enhance cardiac function when the subject is at rest.

In an example, the therapy control circuit 306 can be configured to adjust a therapy for a subject with a cardiac conduction block, such as an RBBB. For example, the therapy control circuit 306 can be configured to deliver a pacing therapy in an RV-only pacing mode. In this example, the intrinsic first AV delay can be determined using a duration between a sensed or paced atrial event and a subsequent sensed event in the LV of the heart 110. The second AV delay can be determined using a duration between a sensed or paced atrial event and a subsequent paced event in the RV of the heart 110, such as when the subject is at rest. In an example, the second AV delay can be determined such that the paced event of the RV is approximately fused with the intrinsic event of the LV of the heart 110, such as when the subject is at rest.

In an example, the therapy control circuit 306 can be configured to receive or determine information indicative of an offset duration between the second AV delay and the intrinsic first AV delay. The offset duration can be indicative of an inter-ventricular delay that can be used to determine an optimal cardiac output of the heart 110, such as when the subject is at rest. In an example, the offset duration can be a difference between the intrinsic first AV delay duration and the second AV delay duration. In an example that includes an LV-only pacing mode, the offset duration can be indicative of an RV-LV inter-ventricular delay. In an example that includes an RV-only pacing mode, the offset duration can be indicative of an LV-RV inter-ventricular delay.

In an example, the therapy control circuit 306 can be configured to receive information indicative of a heart rate, such as a resting heart rate or a non-resting heart rate. In an example, the heart rate can be determined using the heart rate sensor 312 or derived using the pressure sensor 314, among other techniques. In an example, the physiologic parameter sensing circuit 310 can be configured to provide information indicative of a subject heart rate to the therapy control circuit 306.

A change in a subject heart rate can correspond to a change in the subject's intrinsic AV delay. For example, an intrinsic AV delay can vary when a subject is engaged in a physical activity that can substantially increase or decrease the heart rate of the subject. In an example, the therapy control circuit 306 can be configured to receive a heart rate dependent AV delay 316 for a non-resting state of the subject. In the example of an LV-only pacing mode, the heart rate dependent AV delay 316 can correspond to a duration between a paced or sensed event in the atrium and a later sensed event in the RV of the heart 110, such as when the subject is in a non-resting state. In the example of an RV-only pacing mode, the heart rate dependent AV delay 316 can correspond to a duration between a paced or sensed event in the atrium and a later sensed event in the LV of the heart 110, such as when the subject is in a non-resting state.

Figure 4:
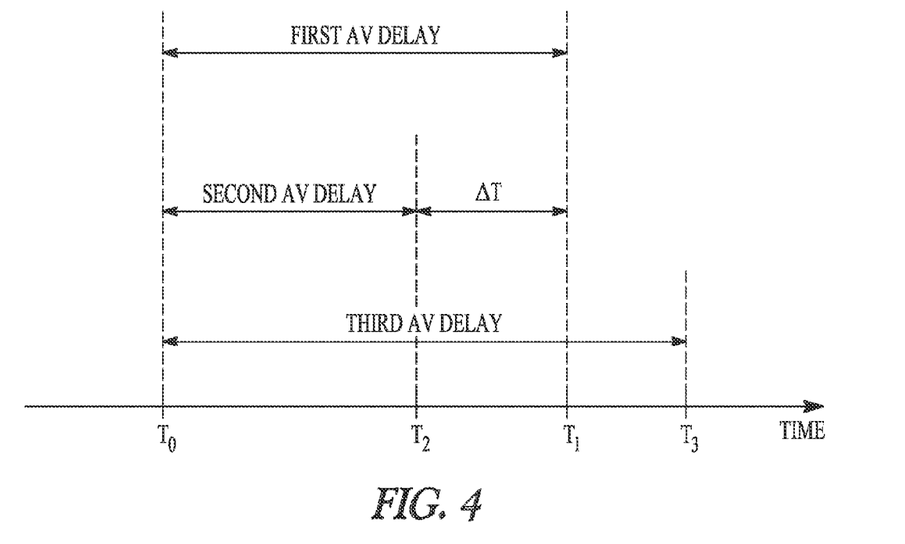
FIG. 4 illustrates generally an example of atrioventricular delay timing.

FIG. 4 illustrates generally examples of timings associated with a pacing therapy, such as a therapy configured to treat a bundle branch block. In the example of FIG. 4, $T_0$ indicates a time of a sensed or paced atrial event. $T_1$ indicates a time associated with a sensed event in a first ventricle (e.g., RV) and $T_2$ indicates a timing associated with a paced event in a second ventricle (e.g., LV) of the heart 110, such as when the subject is at rest. In an example, the intrinsic first AV delay can be determined from differences in timings of an atrial event and events in the first and second ventricles. The offset duration between $T_2$ and $T_1$ is $\Delta T$. In the example of FIG. 4, $T_3$ indicates a time associated with a heart rate dependent AV delay 316.

In an example, the therapy control circuit 306 can be configured to adjust a therapy using information about the subject heart rate, the heart rate dependent AV delay 316 and an offset duration (e.g., $\Delta T$ in the example of FIG. 4). In an example, the therapy control circuit 306 can be configured to adjust a single-ventricle-only pacing therapy, wherein the therapy control circuit 306 can be configured to adjust an AV delay using information about a heart rate of a subject. In an example that can include an LV-only pacing mode, the therapy control circuit 306 can be configured to control a pacing therapy delivered to the LV of the heart 110 using the heart rate dependent AV delay 316 such that the LV activation can be fused with the intrinsic RV activation, such as when the subject is in resting or non-resting states. In an example that can include an RV-only pacing mode, the therapy control circuit 306 can be configured to control a pacing therapy delivered to the RV of the heart 110 using the heart rate dependent AV delay 316 such that the RV activation can be fused with the intrinsic LV activation, such as when the subject is in resting or non-resting states.

In an example, a pacing therapy, such as an LV-only pacing therapy or an RV-only pacing therapy, among others, can be updated using information about a heart rate dependent AV delay. For example, an AV delay can be dynamically updated to accommodate a change in AV delay, such as can correspond to a change in a subject heart rate. In an example, AV delay information can be received or determined about a particular subject or population, such as including information about corresponding heart rates and AV delays. The information can be used (e.g., by the CRM system 100) to implement enhanced therapies, such as to improve patient cardiac output in the presence of a cardiac conduction block. In an example, predefined, or premeasured AV delay information can be stored, such as in the memory circuit 304 of the IMD 102, or in an external programmer communicatively coupled to the IMD 102. In an example, such predefined AV delay information can be stored in a lookup table.

Figure 5:
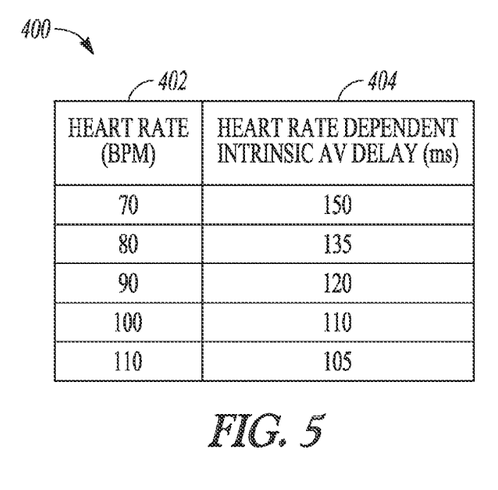
FIG. 5 illustrates generally an example of a lookup table with corresponding heart rate information and atrioventricular delay information.

FIG. 5 illustrates generally an example of a lookup table 400 that includes corresponding information about heart rate and intrinsic AV delay duration. In an example, the lookup table 400 can include subject-specific, heart rate dependent intrinsic AV delay information with corresponding subject-specific heart rate information. In an example, the lookup table 400 can include multiple rows and columns, such as including a first column 402 with values indicative of subject heart rates, and a second column 404 with corresponding values indicative of intrinsic AV delays. In an example, the intrinsic heart rate dependent AV delay durations can be determined by monitoring a subject heart rate, such as over a specified duration. In the example of FIG. 5, the lookup table 400 indicates that a particular subject can have an intrinsic AV delay of about 120 ms at a heart rate of about 90 bpm. In an example, the lookup table 400 can be updated, such as at regular intervals (e.g., daily, monthly, etc.) or in response to an update request (e.g., by a clinician). In an example, the therapy control circuit 306 can be configured to receive information about a current heart rate of a subject using the physiologic parameter sensing circuit 310, and access the lookup table 400 in the memory circuit 304, such as to retrieve information about a subject-specific intrinsic AV delay that corresponds to the current heart rate. The therapy control circuit 306 can be configured to use the retrieved intrinsic AV delay information corresponding to the current heart rate of the subject to initiate or adjust a pacing therapy.

Figure 6:
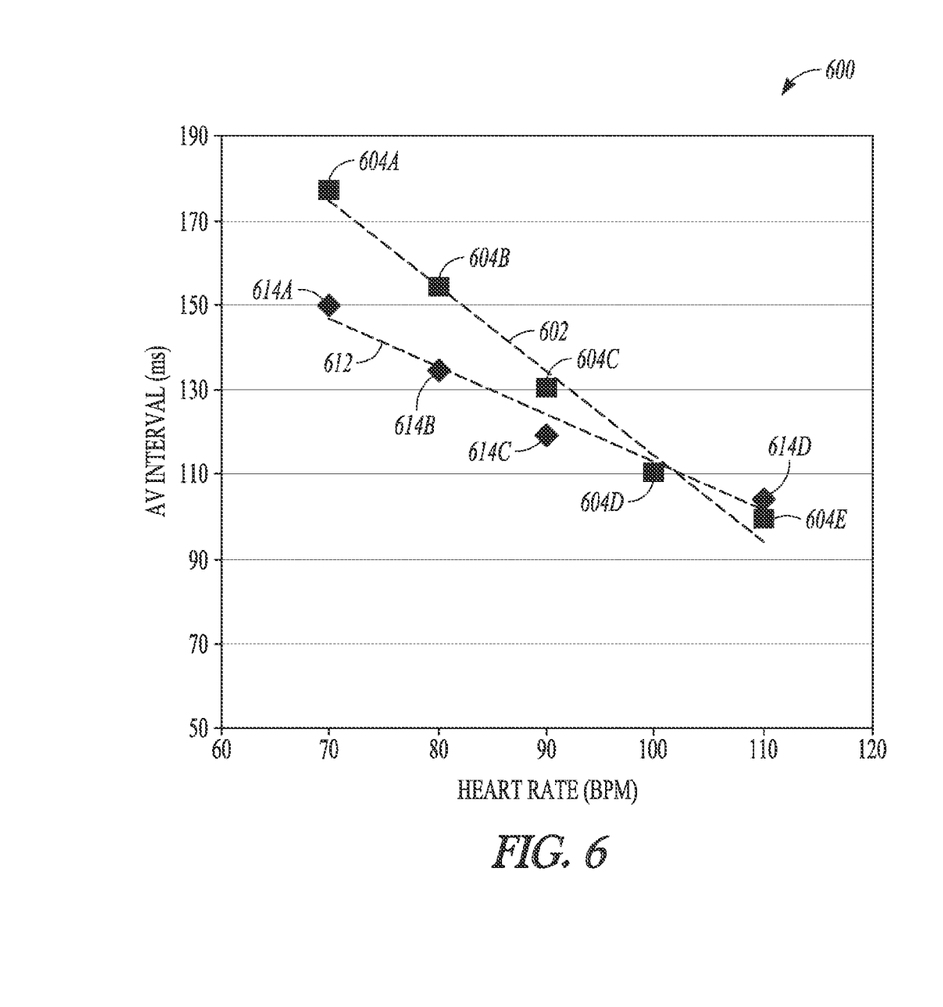
FIG. 6 illustrates generally an example of a relationship between heart rate and atrioventricular delay.

FIG. 6 illustrates generally an example of a graph 600 of a relationship between heart rate and intrinsic AV delay. In an example, the graph 600 can include subject or population-specific heart rate and AV delay information, or a combination thereof. The example of FIG. 6 includes a first restitution curve 602 and a second restitution curve 612. The restitution curves 602 and 612 can indicate a pattern or trend of intrinsic AV delay, such as at various heart rates of one or more subjects. In an example, a restitution curve can be determined by plotting two or more values of an intrinsic AV delay (e.g., a subject-specific intrinsic AV delay) and corresponding heart rate information. For example, the first restitution curve 602 can be determined using several plotted values (e.g., values 604a, 604b, 604c, 604d, and 604e) and the second restitution curve 612 can be constructed using several other values (e.g., values 614a, 614b, 614c, and 614d). In an example, the lookup table 400 can be used to provide corresponding heart rate and intrinsic AV delay information. In an example, the first restitution curve 602 can correspond to a first patient or first patient population, and the second restitution curve 612 can correspond to a different second patient or second patient population (e.g., a second population that has no members in common with the first population of patients).

In an example, a restitution function can be determined using AV delay and heart rate information, such as using information from a restitution curve. In an example, a restitution function can be a subject-specific, intrinsic AV delay restitution function that provides subject-specific information about an AV delay at various heart rates. For example, a first restitution function corresponding to the first restitution curve 602 can be a linear function, such as represented by the function $y=-2x+316$, where y is the AV delay and x is the heart rate. Similarly, a second restitution function corresponding to the second restitution curve 612 can be a linear function, such as represented by the function $y=-1.2x+228$. In an example, the memory circuit 304 can be configured to store values of the heart rate dependent AV delay 316 in the form of a restitution function. In an example, the therapy control circuit 306 can be configured to receive heart rate information, such as using the physiologic parameter sensing circuit 310, and access the memory circuit 304, such as to retrieve a subject-specific restitution function. In an example, the therapy control circuit 306 can be configured to use the processor circuit 302 to determine a therapy AV delay using the retrieved restitution function and received heart rate information. The therapy control circuit 306 can be configured to use an AV delay determined using the restitution function to adjust a pacing therapy.

Figure 7:
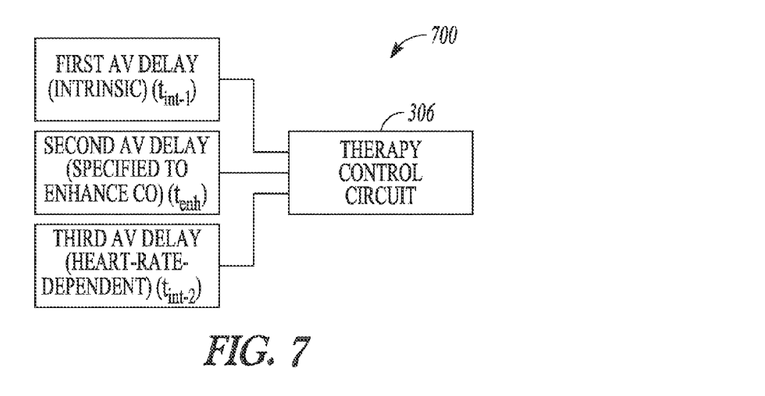
FIG. 7 illustrates generally an example of a therapy control circuit.
Figure 8:
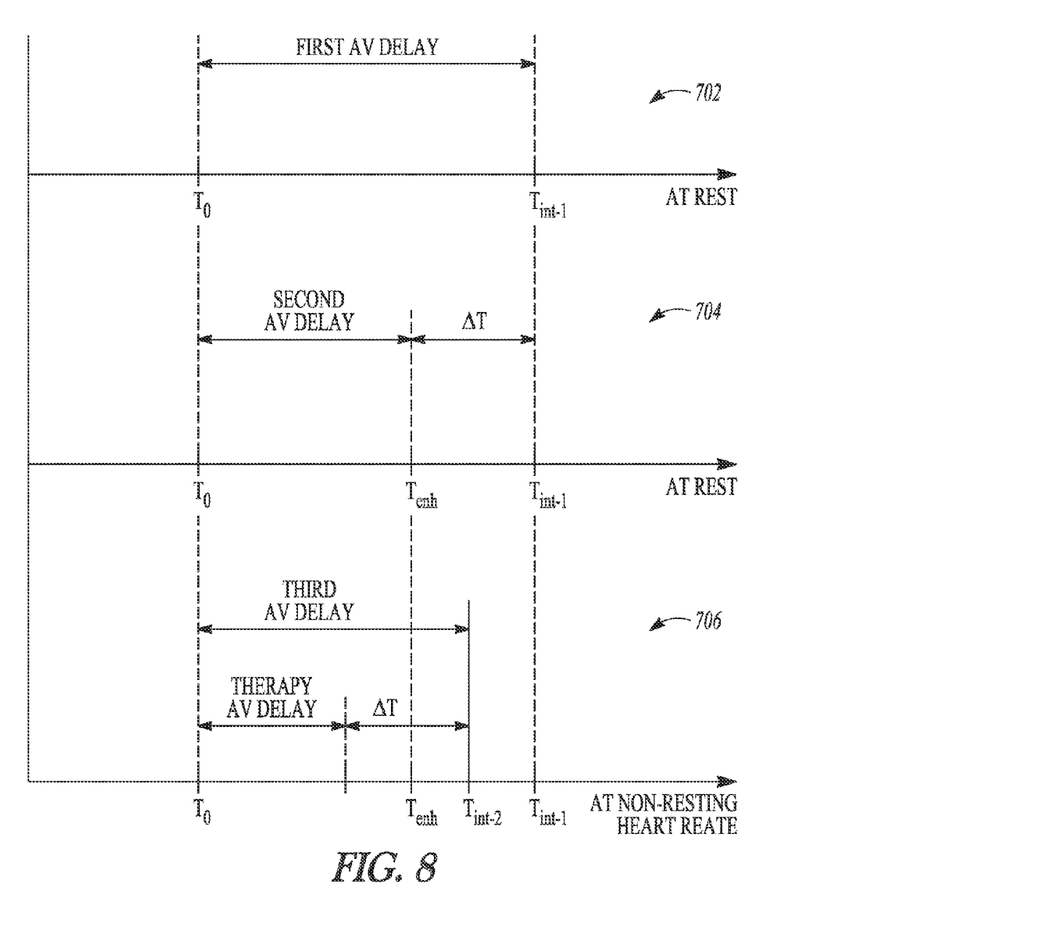
FIG. 8 illustrates generally an example of atrioventricular delay timing.

Turning now to FIGS. 7 and 8, FIG. 7 illustrates generally an example 700 of the therapy control circuit 306, such as can be configured to compute a therapy AV delay for a pacing therapy. FIG. 8 illustrates examples of relative activation timings used to compute a therapy AV delay, such as for adjusting a single-ventricle-only pacing therapy.

In an example that includes an LV-only pacing therapy, the therapy control circuit 306 can be configured to initiate or adjust a pacing therapy delivered to the LV of the heart 110, and to determine an AV delay (e.g., an intrinsic AV delay) using information about RV activity. In an example, the therapy control circuit 306 can be configured to determine an intrinsic first AV delay as a duration between a paced or sensed atrial event and a subsequent sensed event in the RV of the heart 110, such as when the subject is at rest. As shown in FIG. 8, a first portion 702 of the timing diagram illustrates generally an indication of an atrial event at time $T_0$, and a subsequent intrinsic event (e.g., in the RV of the heart 110) at time $T_{int-1}$. The intrinsic first AV delay can be determined to be the duration difference between $T_0$ and $T_{int-1}$ (i.e., $T_{int-1}-T_0$).

In an example, the therapy control circuit 306 can be configured to control a pacing therapy to optimize cardiac output of the heart 110, such as to address a dyssynchrony between left and right sides of the heart 110. In an example, early activation of a ventricle (e.g., early activation of the LV in the presence of LBBB) can improve cardiac output of the heart 110. Accordingly, in an example, the therapy control circuit 306 can be configured to deliver an electrostimulation signal to the heart 110 (e.g., to the left ventricle) at an interval (e.g., the second AV delay) that can be shorter than the intrinsic LV activation interval, such as to enhance cardiac output of the heart 110. In an example, the second AV delay can be an optimized delay parameter, such as can be determined manually, such as using information about mitral flow from Doppler echocardiography, or using information about heart chamber pressure, such as received from a pressure catheter disposed in the LV of the heart 110. In an example, other methods or devices can be used to determine the second AV delay.

In an example, the second AV delay can be a duration between a paced or sensed event in an atrium and a paced event in a ventricle (e.g., in the LV) of the heart 110, such as when the subject is at rest. As illustrated in the example of FIG. 7, a second portion 704 of the timing diagram indicates a relative timing of a paced event in a ventricle of the heart 110 as $T_{enh}$ when the subject is at rest. That is, $T_{enh}$ can correspond to a calculated or otherwise determined time interval configured to enhance cardiac output of the heart 110. In the example of FIG. 8, the second portion 704 of the timing diagram illustrates generally that the second AV delay, corresponding to the $T_0$ to $T_{enh}$ interval, can be a lesser duration than the intrinsic first AV delay. In an example, the second AV delay can be a longer duration than the intrinsic first AV delay.

In an example, the therapy control circuit 306 can be configured to compute a duration difference between the second AV delay and the intrinsic first AV delay (i.e., $T_{enh}-T_{int-1}$). This duration difference can be an offset duration, and it can indicate an inter-ventricular AV delay that can be used to adjust a pacing therapy. The offset duration is illustrated in the example of FIG. 8 as $\Delta T$ (e.g., in the second portion 704 of the timing diagram). In an example, the offset duration can have a negative or positive value. That is, the offset duration can be a positive value when the second AV delay is a shorter duration than the intrinsic first AV delay, and the offset duration can be a positive value when the second AV delay is greater than the intrinsic first AV delay. The second portion 704 of the timing diagram indicates a negative offset value because, in the example of FIG. 8, the duration of the second AV delay is less than the duration of the intrinsic first AV delay.

In an example, the therapy control circuit 306 can be configured to receive information indicative of a subject heart rate and retrieve or determine an intrinsic third AV delay of the subject, such as an AV delay corresponding to a particular subject heart rate (e.g., corresponding to a non-resting subject heart rate). The intrinsic third AV delay can correspond to a duration between a paced or sensed event in an atrium and a later sensed event in a ventricle (e.g., in the RV) of the heart 110, such as at a specified subject heart rate. In an example, the intrinsic third AV delay can be retrieved from the memory circuit 304 of the IMD 102, e.g., using a lookup table or a restitution function. In an example, a third portion 706 of the timing diagram of FIG. 7 illustrates generally a tinning of an intrinsic third AV delay as a duration between $T_0$ and $T_{int-2}$.

In an example, the therapy control circuit 306 can be configured to adjust a pacing therapy (e.g., an LV-only pacing therapy) using the offset duration ($\Delta T$) and the intrinsic third AV delay. In this manner, the therapy control circuit 306 can be configured to compute a therapy AV delay configured to enhance cardiac output of a subject at a non-resting heart rate, such as using information about an offset duration ($\Delta T$) determined using AV delay information corresponding to the subject resting heart rate. In an example, the therapy AV delay can correspond to an interval from a sensed or paced atrial event to a paced event in the LV of the patient at the non-resting heart rate. In an example, the therapy control circuit 306 can be configured to compute the therapy AV delay as a sum of the offset duration and the intrinsic third AV delay. In an example, the therapy AV delay can be used in a pacing therapy to treat a bundle branch block, such as a left bundle branch block, such as to enhance a subject cardiac output at resting and non-resting heart rates, such as by fusing paced ventricular events with intrinsic cardiac events.

Figure 9:
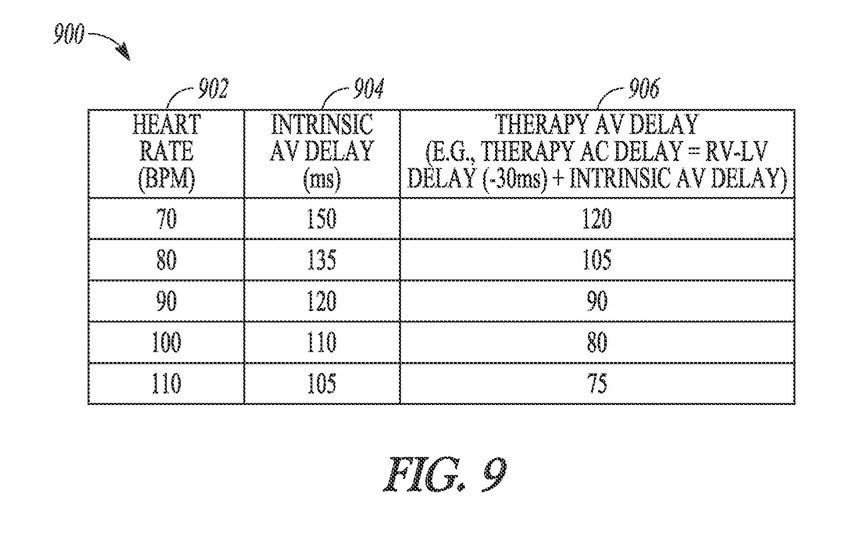
FIG. 9 illustrates generally an example of a table with corresponding heart rate information, intrinsic atrioventricular delay information, and therapy atrioventricular delay information.

FIG. 9 illustrates generally an example of a table 900 that shows corresponding therapy AV delay information, intrinsic AV delay information, and heart rate information. Column 902 of the table 900 corresponds to the column 402 of the table 400, and includes information about various heart rates (e.g., of a particular subject). Column 904 of the table 900 corresponds to the column 404 of the table 400, and includes information about intrinsic AV delays, such as corresponding to the heart rates in the column 902. In an example, the therapy control circuit 306 can be configured to compute an offset duration or an inter-ventricular delay, such as using an intrinsic AV delay (e.g., $T_{int-1}$) and the enhanced AV delay (e.g., $T_{enh}$), such as when the subject is at rest. In the example of FIG. 9, the table 900 indicates an inter-ventricular delay of –30 ms. Column 906 of the table 900 includes computed therapy AV delay durations that correspond to the heart rates listed in column 902. In an example, the therapy control circuit 306 can be configured to select a particular therapy AV delay that corresponds to a subject heart rate, such as using the table 900. In an example, the therapy control circuit 306 can be configured to compute an AV delay corresponding to a specified heart rate using an AV delay restitution function, and then to compute a therapy AV delay at the specified heart rate.

Figure 10:
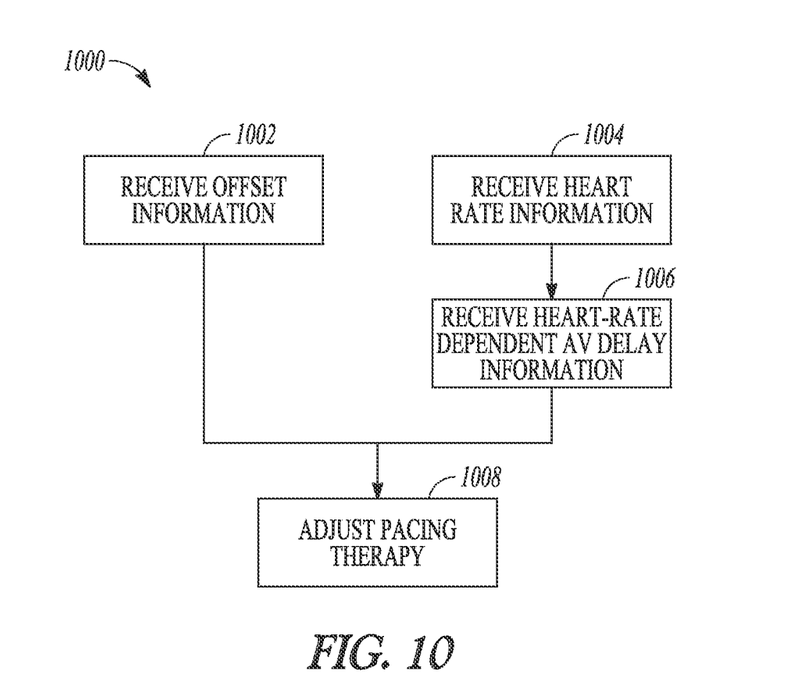
FIG. 10 illustrates generally an example that can include adjusting a subject therapy.

FIG. 10 illustrates generally an example 1000 of a method that can include adjusting a pacing therapy. In an example, a pacing therapy can be delivered to treat a cardiac conduction dysfunction, such as to treat LBBB or RBBB. In an example, a pacing therapy can be optimized for a left-ventricle only pacing therapy to improve cardiac output in the presence of an LBBB.

At 1002, information indicative of an offset duration can be received. The offset duration can be indicative of an inter-ventricular delay of the heart 110, such as when the subject is at rest. In an example, the offset duration can correspond to a duration difference between an intrinsic first AV delay and a second. AV delay specified to enhance a subject's cardiac output when the subject is at rest. In an example, the information indicative of an offset duration can be received using the processor circuit 302, the memory circuit 304, or the therapy control circuit 306. At 1004, heart rate information can be received, such as including subject-specific heart rate information received using the physiologic parameter sensing circuit 310. The received heart rate information can include information about a non-resting heart rate of a subject. In an example, the heart rate can be determined using the heart rate sensor 312 or derived from the pressure sensor 314.

At 1006, information about a heart rate dependent AV delay can be received. In an example, the heart rate dependent AV delay 316 can be received via the memory circuit 304. The heart rate dependent AV delay can include information about an AV delay duration that corresponds to one or more subject heart rates.

At 1008, a pacing therapy can be adjusted using the received offset information, the received heart rate information, and the received heart rate dependent AV delay information. In an example, adjusting the pacing therapy at 1008 can include adjusting an AV delay parameter corresponding to a single-ventricle-only pacing therapy. In an example, a pacing therapy can be adjusted to enhance or improve fusion of a first ventricle depolarization with a second ventricle depolarization, and thereby improve cardiac output.

Figure 11:
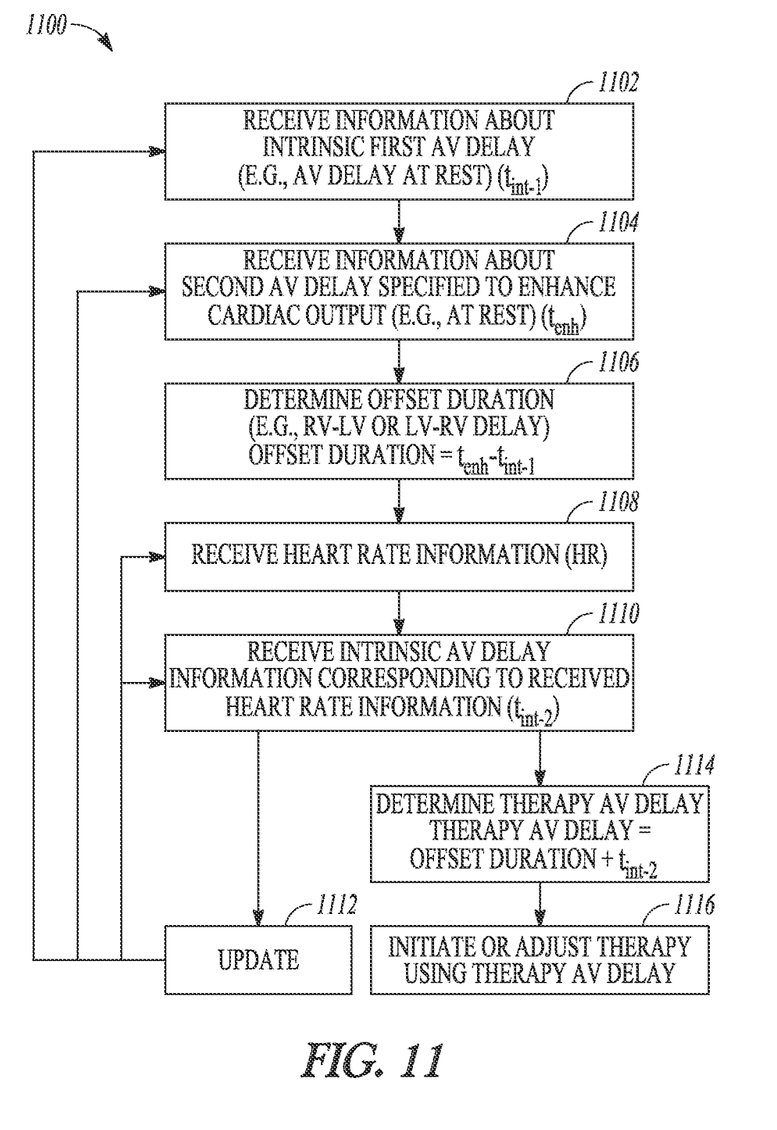
FIG. 11 illustrates generally an example that can include adjusting a subject therapy.

FIG. 11 illustrates generally an example 1100 that can include initiating or adjusting a therapy using a therapy AV delay parameter. At 1102, information about an intrinsic first AV delay (e.g., $T_{int-1}$ in the example of FIG. 8) can be received, such as including information about an intrinsic AV delay when a subject is at rest. In an example of an LV-only pacing mode, $T_{int-1}$ can indicate a delay duration corresponding to a sensed right ventricular event following a paced or sensed atrial event. In an example of an RV-only pacing mode, $T_{int-1}$ can indicate a delay duration corresponding to a sensed left ventricular event following a paced or sensed atrial event.

At 1104, the information about second AV delay (e.g., $T_{enh}$ in the example of FIG. 8) can be received. In an example, the second AV delay can be specified to enhance cardiac output of the heart 110, such as when the subject is at rest. In an example that includes an LV-only pacing mode, $T_{enh}$ can indicate a delay duration corresponding to a paced left ventricular event that follows a paced or sensed atrial event. In an example that includes an RV-only pacing mode, $T_{enh}$ can indicate a delay duration corresponding to a paced right ventricular event following a paced or sensed atrial event. In an example, the second AV delay can be specified to optimize or enhance fusion of the paced activation of a ventricle (e.g., LV) with intrinsic activation of the second ventricle (RV).

At 1106, an offset duration can be determined. The offset duration can be determined using the received information about the intrinsic first AV delay (e.g., received at 1102) and using the received information about the second AV delay specified to enhance cardiac output (e.g., received at 1104). In an example, the offset duration can be determined using the processor circuit 302 or the therapy control circuit 306. In an example, the offset duration can correspond to an inter-ventricular delay that can be used to enhance cardiac output of the heart 110 over a range of subject heart rates.

In an example, the inter-ventricular delay can correspond to a duration difference between a sensed RV event and a paced LV event in an LV-only pacing mode, or the inter-ventricular delay can correspond to a duration difference between a sensed LV event and a paced RV event in an RV-only pacing mode. In an example, the offset duration can be determined as a duration difference between the second AV delay and the intrinsic first AV delay. That is, the offset duration can be calculated (e,g., at 1106) as $T_{enh}-T_{int-1}$. At 1108, information about a subject heart rate can be received, such as using the physiologic parameter sensing circuit 310. In an example, the information about, the heart rate can include information about a non-resting heart rate of the subject.

At 1110, intrinsic AV delay information (e.g., $T_{int-2}$) corresponding to a heart rate can be received. In an example, a heart rate dependent intrinsic AV delay can be retrieved from the memory circuit 304 of the IMD 102. The heart rate dependent AV delay can correspond to a duration between a paced or sensed atrial event and a sensed ventricular event at a particular heart rate. In an example, at 1112, one or more AV delay parameters or measurements can be updated, or a heart rate can be received. For example, the intrinsic first AV delay or second AV delay, such as corresponding to a subject at rest, can be updated. In an example, the update at 1112 can be initiated automatically or manually, such as by a physician, or after an occurrence of a specified event. In an example, heart rate information or information about corresponding intrinsic AV delays can be updated. In an example, the update at 1112 can include an update of the lookup table 400 or of a subject-specific AV delay restitution function.

At 1114, a therapy AV delay can be determined using the offset duration and the heart rate dependent AV delay, such as using the processor circuit 302 or the therapy control circuit 306. In an example, the therapy AV delay can be calculated as a sum of the offset duration and the heart rate dependent AV delay (e.g., $T_{int-2}$). At 1116, a pacing therapy can be initiated or adjusted using the computed therapy AV delay and the therapy control circuit 306. In an example, the therapy AV delay can be used for adjusting or initiating a single-ventricle-only pacing therapy such as to optimally fuse a pacing therapy with a native activation of the heart 110. Such fusion therapy can provide a relatively long time for blood to fill a left ventricle, and can improve coordination between the ventricles of the heart 110, such as to provide improved cardiac output of the heart 110.

VARIOUS NOTES AND EXAMPLES

Example 1 can include or use subject matter such as an apparatus, method, a means for performing acts, or a device readable medium including instructions that, when performed by the device, can cause the device to perform acts, such as can include or use a system comprising a therapy control circuit. The therapy control circuit can be configured to receive information indicative of an offset duration that defines a duration difference between an intrinsic first atrio-ventricular (AV) delay of a subject at rest and a second AV delay specified to enhance a cardiac output of a subject heart when the subject is at rest. The therapy control circuit can be configured to receive information about a heart rate of the subject, and adjust a pacing therapy using information about the received heart rate of the subject, a heart-rate-dependent third AV delay, and the offset duration.

Example 2 can include, or can optionally be combined with the subject matter of Example 1, to optionally include the therapy control circuit configured to receive information indicative of the second AV delay, the second AV delay specified to enhance a cardiac output of a subject heart when the subject is at rest. In Example 2, the second AV delay defines a duration between a paced or sensed atrial event and a paced ventricular event.

Example 3 can include, or can optionally be combined with the subject matter of one or any combination of Examples 1 or 2 to optionally include the therapy control circuit configured to update the information indicative of the second AV delay in response to a subject physiologic event or in response to a threshold change in a subject physiologic status.

Example 4 can include, or can optionally be combined with the subject matter of one or any combination of Examples 1 through 3 to optionally include, as the intrinsic first AV delay of the subject at rest, a duration between a paced or sensed event in an atrium and a later sensed event in a first ventricle. In Example 4, the second AV delay specified to enhance the cardiac output of the subject heart when the subject is at rest can correspond to a duration between a paced or sensed event in the atrium and a later event in a second ventricle.

Example 5 can include, or can optionally be combined with the subject matter of Example 4 to optionally include, as the intrinsic first AV delay of the subject at rest, a duration between a paced or sensed event in an atrium and a later sensed event in a right ventricle, and include, as the second AV delay specified to enhance the cardiac output of the subject heart when the subject is at rest, a duration between a paced or sensed event in the atrium and a later event in a left ventricle.

Example 6 can include, or can optionally be combined with the subject matter of Example 5 to optionally include, as the heart-rate-dependent third AV delay, a duration between a paced or sensed event in the atrium and a later sensed event in the right ventricle.

Example 7 can include, or can optionally be combined with the subject matter of Example 4 to optionally include, as the intrinsic first AV delay of the subject at rest, a duration between a paced or sensed event in an atrium and a later sensed event in a left ventricle, and include, as the second AV delay specified to enhance the cardiac output of the subject heart when the subject is at rest, a duration between a paced or sensed event in the atrium and a later event in a right ventricle.

Example 8 can include, or can optionally be combined with the subject matter of Example 7 to optionally include, as the heart-rate-dependent third AV delay, a duration between a paced or sensed event in the atrium and a later sensed event in the left ventricle.

Example 9 can include, or can optionally be combined with the subject matter of one or any combination of Examples 1 through 8 to optionally include the therapy control circuit configured to adjust a single-ventricle-only pacing therapy using the information about the received heart rate of the subject, the heart-rate-dependent third AV delay, and the offset duration.

Example 10 can include, or can optionally be combined with the subject matter of one or any combination of Examples 1 through 9 to optionally include the therapy control circuit configured to adjust the pacing therapy using an enhanced AV delay comprising a sum of the heart-rate-dependent third AV delay and the offset duration.

Example 11 can include, or can optionally be combined with the subject matter of Example 10 to optionally include, as the enhanced AV delay, a duration between a paced or sensed atrial event and a left ventricle pace event.

Example 12 can include, or can optionally be combined with the subject matter of Example 10 to optionally include, as the enhanced AV delay, a duration between a paced or sensed atrial event and a right ventricle pace event.

Example 13 can include, or can optionally be combined with the subject matter of one or any combination of Examples 1 through 12 to optionally include the therapy control circuit configured to adjust the pacing therapy using the information about the heart-rate-dependent third AV delay, including receiving the information about the heart-rate-dependent third AV delay from a lookup table, the lookup table comprising corresponding heart rate and intrinsic AV delay information.

Example 14 can include, or can optionally be combined with the subject matter of one or any combination of Examples 1 through 13 to optionally include the therapy control circuit configured to adjust the pacing therapy using an intrinsic AV delay restitution function to provide information about the heart-rate-dependent third AV delay.

Example 15 can include, or can optionally be combined with the subject matter of Example 14 to optionally include, as the intrinsic AV delay restitution function, a subject-specific restitution function that provides subject-specific information about intrinsic AV delay at multiple heart rates.

Example 16 can include, or can optionally be combined with the subject matter of one or any combination of Examples 1 through 15 to optionally include the therapy control circuit configured to receive information about a non-resting heart rate of the subject. In Example 16, the therapy control circuit can be configured to adjust the pacing therapy using the offset duration and a heart-rate-dependent third AV delay that corresponds to the non-resting heart rate of the subject.

Example 17 can include, or can optionally be combined with the subject matter of one or any combination of Examples 1 through 16 to optionally include the therapy control circuit configured to receive, as the information indicative of the offset duration, information indicative of one of an RV-LV interventricular delay or an LV-RV interventricular delay.

Example 18 can include, or can optionally be combined with the subject matter of one or any combination of Examples 1 through 17 to optionally include a physiologic parameter sensing circuit, such as can be coupled to a pressure catheter disposed in a ventricle of the subject heart. In Example 18, the therapy control circuit can be configured to determine the second AV delay specified to enhance the cardiac output of the subject heart when the subject is at rest using information received from the pressure catheter.

Example 19 can include, or can optionally be combined with the subject matter of one or any combination of Examples 1 through 18 to optionally include determining the second AV delay specified to enhance the cardiac output of the subject heart when the subject is at rest using Doppler echocardiography.

Example 20 can include or use subject matter such as an apparatus, a method, a means for performing acts, or a device readable medium including instructions that, when performed by the device, can cause the device to perform acts, such as can include or use a therapy control circuit, a therapy output circuit coupled to the therapy control circuit and configured to generate a pacing therapy, the therapy output circuit coupleable to a therapy delivery electrode, and a physiologic parameter sensing circuit configured to receive information indicative of a subject heart rate. In Example 20, the therapy control circuit can be configured to receive information indicative of an offset duration defining a duration difference between an intrinsic first atrioventricular (AV) delay of a subject at rest and a second AV delay specified to enhance a cardiac output of a subject heart when the subject is at rest. In Example 20, the therapy control circuit can be configured to receive information indicative of a subject heart rate. In Example 20, the therapy control circuit can be configured to adjust the pacing therapy generated by the therapy output circuit using the information about the subject heart rate, a heart-rate-dependent third AV delay, and the offset duration.

Example 21 can include, or can optionally be combined with the subject matter of Example 20 to optionally include the therapy control circuit configured to receive information indicative of the second AV delay, the second AV delay specified to enhance a cardiac output of a subject heart when the subject is at rest, and the second AV delay defining a duration between a paced or sensed atrial event and a paced event in a first ventricle, the paced event in the first ventricle approximately fused with an intrinsic event in a second ventricle.

Example 22 can include, or can optionally be combined with the subject matter of one or any combination of Examples 20 or 21 to optionally include the therapy delivery electrode, wherein the therapy delivery electrode is disposed in a left ventricle of the subject heart, and wherein the therapy output circuit is configured to provide the pacing therapy to the therapy delivery electrode disposed in the left ventricle of the subject heart.

Example 23 can include, or can optionally be combined with the subject matter of one or any combination of Examples 20 through 22 to optionally include the therapy delivery electrode, wherein the therapy delivery electrode is disposed in a right ventricle of the subject heart, and wherein the therapy output circuit is configured to provide the pacing therapy to the therapy delivery electrode disposed in the right ventricle of the subject heart.

Example 24 can include, or can optionally be combined with the subject matter of one or any combination of Examples 20 through 23 to optionally include a first therapy delivery electrode disposed in an atrium of the subject heart, a second therapy delivery electrode disposed in a left ventricle of the subject heart, and a third therapy delivery electrode disposed in a right ventricle of the subject heart.

Example 25 can include or use subject matter such as an apparatus, a method, a means for performing acts, or a device readable medium including instructions that, when performed by the device, can cause the device to perform acts, such as can include or use a therapy control circuit, a therapy output circuit, and a physiologic parameter sensing circuit. In Example 25, the therapy output circuit can be coupled to the therapy control circuit and configured to generate a pacing therapy, and the therapy output circuit can be coupleable to a therapy delivery electrode. In Example 25, the physiologic parameter sensing circuit can be configured to receive information indicative of a subject heart rate. In Example 25, the therapy control circuit can use an intrinsic first atrioventricular (AV) delay of a subject at rest, a second AV delay specified to enhance a cardiac output of a subject heart when the subject is at rest, and a heart-rate-dependent third AV delay to instruct the therapy output circuit to generate the pacing therapy. In Example 25, the therapy control circuit can be configured to receive information indicative of the second AV delay, the second AV delay specified to enhance a cardiac output of a subject heart when the subject is at rest, and the second AV delay defining a duration between a paced or sensed event in an atrium of the subject heart and a paced event in a left ventricle of the subject heart. In Example 25, the therapy control circuit can be configured to receive information indicative of an offset duration defining a duration difference between an intrinsic first atrioventricular (AV) delay of a subject at rest and a second AV delay specified to enhance a cardiac output of a subject heart when the subject is at rest, wherein the intrinsic first AV delay corresponds to a duration between a paced or sensed event in the atrium of the subject heart and a later sensed event in a right ventricle of the subject heart. In Example 25, the therapy control circuit can be configured to receive information indicative of a subject heart rate, and adjust the pacing therapy generated by the therapy output circuit using the information about the subject heart rate, a heart-rate-dependent third AV delay, and the offset duration, wherein the heart-rate-dependent third AV delay corresponds to a duration between a paced or sensed event in the atrium of the subject heart and a later sensed event in the right ventricle of the subject heart.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. section 1.72(b), to allow the reader to quickly ascertain the nature of the technical disclosure, it is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system comprising:
a therapy control circuit configured to:
receive information indicative of an offset duration defining a duration difference between an intrinsic first atrioventricular (AV) delay of a subject at rest and a second AV delay specified to enhance a cardiac output of a subject heart when the subject is at rest, the intrinsic first AV delay defining a duration between a paced or sensed event in an atrium of the subject heart and a sensed event in a ventricle of the subject heart, and the second AV delay defining a duration between a paced or sensed event in an atrium of the subject heart and a paced event in a ventricle of the subject heart;
receive information about a heart rate of the subject; and
adjust a pacing therapy using information about the received ea rate of the subject, a heart-rate-dependent third. AV delay, and the offset duration.

2. The system of claim 1, wherein the therapy control circuit is configured to receive information indicative of the first and second AV delays.

3. The system of claim 1, wherein the therapy control circuit is configured to update the information indicative of the second AV delay in response to a subject physiologic event or in response to a threshold change in a subject physiologic status.

4. The system of claim 1, wherein the intrinsic first AV delay of the subject at rest corresponds to a duration between a paced or sensed event in an atrium and a later sensed event in a first ventricle, and wherein the second. AV delay specified to enhance the cardiac output of the subject heart when the subject is at rest corresponds to a duration between a paced or sensed event in the atrium and a later event in a second ventricle.

5. The system of claim 4, wherein the intrinsic first AV delay of the subject at rest corresponds to a duration between a paced or sensed event in an atrium and a later sensed event in a right ventricle, and wherein the second AV delay specified to enhance the cardiac output of the subject heart when the subject is at rest corresponds to a duration between a paced or sensed event in the atrium and a later event in a left ventricle.

6. The system of claim 5, wherein the heart-rate-dependent third AV delay corresponds to a duration between a paced or sensed event in the atrium and a later sensed event in the right ventricle.

7. The system of claim 4, wherein the intrinsic first AV delay of the subject at rest corresponds to a duration between a paced or sensed event in an atrium and a later sensed event in a left ventricle, and wherein the second AV delay specified to enhance the cardiac output of the subject heart when the subject is at rest corresponds to a duration between a paced or sensed event in the atrium and a later event in a right ventricle.

8. The system of claim 7, wherein the heart-rate-dependent third AV delay corresponds to a duration between a paced or sensed event in the atrium and a later sensed event in the left ventricle.

9. The system of claim 1, wherein the therapy control circuit is configured to adjust a single-ventricle-only pacing therapy using the information about the received heart rate of the subject, the heart-rate-dependent third AV delay, and the offset duration.

10. The system of claim 1, wherein the therapy control circuit is configured to adjust the pacing therapy using an enhanced AV delay comprising a sum of the heart-rate-dependent third AV delay and the offset duration, and wherein the enhanced AV delay defines a duration between a paced or sensed atrial event and a paced ventricular event.

11. The system of claim 1, wherein the therapy control circuit is configured to adjust the pacing therapy using an intrinsic AV delay restitution function to provide information about the heart-rate-dependent third AV delay.

12. The system of claim 11, wherein the intrinsic AV delay restitution function is a subject-specific restitution function that provides subject-specific information about intrinsic AV delay at multiple heart rates.

13. The system of claim 1, wherein the therapy control circuit is configured to receive information about a non-resting heart rate of the subject, and wherein the therapy control circuit is configured to adjust the pacing therapy using the offset duration and a heart-rate-dependent third AV delay that corresponds to the non-resting heart rate of the subject.

14. The system of claim 1, wherein the therapy control circuit is configured to receive, as the information indicative of the offset duration, information indicative of one of an RV-LV interventricular delay or an LV-RV interventricular delay.

15. The system of claim 1, comprising a physiologic parameter sensing circuit coupled to a pressure catheter disposed in a ventricle of the subject heart, wherein the therapy control circuit is configured to determine the second AV delay specified to enhance the cardiac output of the subject heart when the subject is at rest using information received from the pressure catheter.

16. A method of adjusting a pacing therapy, comprising:
receiving information indicative of an offset duration defining a duration difference between an intrinsic first atrioventricular (AV) delay of a subject at rest and a second AV delay specified to enhance a cardiac output of a subject heart when the subject is at rest, the intrinsic first AV delay defining a duration between a paced or sensed event in an atrium of the subject heart and a sensed event in a ventricle of the subject heart, and the second AV delay defining a duration between a paced or sensed event in an atrium of the subject heart and a paced event in a ventricle of the subject heart;
receiving information about a heart rate of the subject; and
adjusting a pacing therapy using information about the received heart rate of the subject, a heart-rate-dependent third AV delay, and the offset duration.

17. The method of claim 16, comprising:
receiving information indicative of the second AV delay, the second AV delay specified To enhance a cardiac output of a subject heart when the subject is at rest, and the second AV delay defining a duration between a paced or sensed atrial event and a paced left ventricular event; and
updating the information indicative of the second AV delay in response to a subject physiologic event or in response to a threshold change in a subject physiologic status.

18. The method of claim 16, wherein the intrinsic first AV delay of the subject at rest corresponds to a duration between a paced or sensed event in an atrium and a later sensed event in a first ventricle, and wherein the second AV delay specified to enhance the cardiac output of the subject heart when the subject is at rest corresponds to a duration between a paced or sensed event in the atrium and a later event in a second ventricle.

19. The method of claim 16, wherein the adjusting the pacing therapy includes using an enhanced AV delay comprising a sum of the heart-rate-dependent third AV delay and the offset duration, and wherein the enhanced AV delay defines a duration between a paced or sensed atrial event and a left ventricle pace event.

20. A system comprising:
   a therapy control circuit;
   a therapy output circuit coupled to the therapy control circuit and configured to generate a pacing therapy, the therapy output circuit coupleable to a therapy delivery electrode; and
   a physiologic parameter sensing circuit configured to receive information indicative of a subject heart rate;
   wherein the therapy control circuit uses an intrinsic first atrioventricular (AV) delay of a subject at rest, a second AV delay specified to enhance a cardiac output of a subject heart when the subject is at rest, and a heart-rate-dependent third AV delay to instruct the therapy output circuit to generate the pacing therapy, wherein the therapy control circuit is configured to:
      receive information indicative of the second AV delay, the second AV delay specified to enhance a cardiac output of a subject heart when the subject is at rest, and the second AV delay defining a duration between a paced or sensed event in an atrium of the subject heart and a paced event in a left ventricle of the subject heart;
      receive information indicative of an offset duration defining a duration difference between an intrinsic first atrioventricular (AV) delay of a subject at rest and a second AV delay specified to enhance a cardiac output of a subject heart when the subject is at rest, wherein the intrinsic first AV delay corresponds to a duration between a paced or sensed event in the atrium of the subject heart and a later sensed event in a right ventricle of the subject heart; receive information indicative of a subject heart rate; and
   adjust the pacing therapy generated by the therapy output circuit using the information about the subject heart rate, a heart-rate-dependent third AV delay, and the offset duration, wherein the heart-rate-dependent third AV delay corresponds to a duration between a paced or sensed event in the atrium of the subject heart and a later sensed event in the right ventricle of the subject heart.

* * * * *